United States Patent [19]

Palta et al.

[11] Patent Number: 5,126,155
[45] Date of Patent: Jun. 30, 1992

[54] PLANT AND FRUIT TREATMENT WITH LYSOPHOSPHATIDYLETHANOLAMINE

[75] Inventors: Jiwan P. Palta; Karim M. Farag, both of Madison, Wis.

[73] Assignee: Wisconsin Alumni Research Foundation, Madison, Wis.

[21] Appl. No.: 785,373

[22] Filed: Oct. 30, 1991

Related U.S. Application Data

[62] Division of Ser. No. 510,650, Apr. 18, 1990.

[51] Int. Cl.⁵ .............................................. A23L 1/212
[52] U.S. Cl. ..................................... 426/331; 426/102; 426/333; 426/615; 426/616; 71/80; 71/86; 71/121
[58] Field of Search ............... 426/331, 333, 102, 615, 426/616, 270

[56] References Cited

U.S. PATENT DOCUMENTS

| | | | |
|---|---|---|---|
| 4,120,970 | 10/1978 | Bice | 426/333 |
| 4,344,971 | 8/1982 | Garbutt | 426/102 |
| 4,647,462 | 3/1987 | Gogins | 426/270 |
| 4,857,344 | 8/1989 | Obrero | 426/333 |
| 4,921,715 | 5/1990 | Nordby | 426/333 |
| 4,990,351 | 2/1991 | Orman | 426/333 |

*Primary Examiner*—Carolyn Paden
*Attorney, Agent, or Firm*—Quarles & Brady

[57] ABSTRACT

Phospholipids in general, and lysophosphatidylethanolamine (LPE) in particular, have been found to be effective agents to enhance the ripening and storage characteristics of fruit, whether applied pre- or post-harvest. LPE both enhances ethylene production in fruit and decreases respiration so as to maintain the fruit firmer for longer. Similar effects occur in leaves and other green plant tissue. Other lysophospholipids and phospholipids with ethanolamine appear to have similar effects.

19 Claims, 1 Drawing Sheet

PLANT AND FRUIT TREATMENT WITH LYSOPHOSPHATIDYLETHANOLAMINE

This is a division of application Ser. No. 07/510,650, filed Apr. 18, 1990.

FIELD OF THE INVENTION

The present invention relates to agents for use in the enhancement or control of fruit ripening and relates, in particular, to a biologically derived agent found useful as a fruit treatment.

BACKGROUND OF THE INVENTION

Various chemical and biological agents are used on commercially grown fruit to control the timing of fruit ripening. Such agents can be used for a variety of purposes. One purpose is to synchronize the ripening of fruit to assist in efficient harvesting of fruit from the field. Another purpose is to prevent drop off of fruit so that fruit remain on the plant or tree until the appropriate ripening time period. Another purpose of fruit ripening agents is to enhance color development in the fruit so that the fruit has a better and more uniform color as expected by retail consumers of the fruit. In the United States, it is current practice for many types of fruit to be treated with one or more such agents during the cultivation process.

Some agents previously used for control of fruit ripening are purely synthetic agents found to have desired effects on the fruit in question. Unfortunately, both due to issues of potential toxicity or oncogenicity, several such synthetic chemical fruit ripening agents have either been banned or had their use sharply curtailed due to commercial or consumer resistance to the products. One well known example of this phenomenon is the chemical Daminozide, sold under the tradename Alar, which was used as a fruit ripening agent on apples until banned in the United States following public controversy regarding potential oncogenicity reported in animal tests. Accordingly, there is a need for such fruit ripening control agents which are not synthetic chemicals in origin but which are biologically derived materials which are much less likely to have any undiscovered carcinogenic effect and which are much more likely to be readily accepted by the commercial interests and the consuming public.

Phosphatidylethanolamine is a fatty acid normally found in lipid layers in biological tissues. It is a phospholipid with two fatty acid groups. It is found abundantly in egg yolk. By the removal of a single fatty acid from phosphatidylethanolamine, lysophosphatidylethanolamine, often referred to below as "LPE," is created. LPE is commercially available from Sigma-Aldrich. LPE is present naturally in small quantities in plant tissues and other biological materials. The quantity of LPE present is increased significantly when natural lipid degradation occurs such as in aging plant tissues.

SUMMARY OF THE INVENTION

The present invention is summarized in that a method for treating fruit to enhance ripening consists of the step of applying to the fruit an effective amount of lysophosphatidylethanolamine sufficient to enhance ripening of the fruit.

The present invention is also directed to the use of LPE as a treatment for green or leafy plant tissue where it has been found to act as a preservative.

It is an object of the present invention to provide a biologically based fruit ripening agent which can be used in field conditions to create desired effect in fruit.

It is an advantage of the present invention in that the fruit ripening agent is a natural biological product derived from materials generally regarded as safe and therefore less likely to have problems associated with carcinogenicity or toxicity.

It is an advantage of the present invention in that the fruit ripening agent disclosed herein can be applied either in field or storage conditions and either to the whole fruit or portions of the fruit to achieve the desired effect on the fruit.

Other objects, advantages, and features of the present invention will become apparent from the following specification when taken in conjunction with the accompanying drawings.

DETAILED DESCRIPTION OF THE INVENTION

Figure 1:
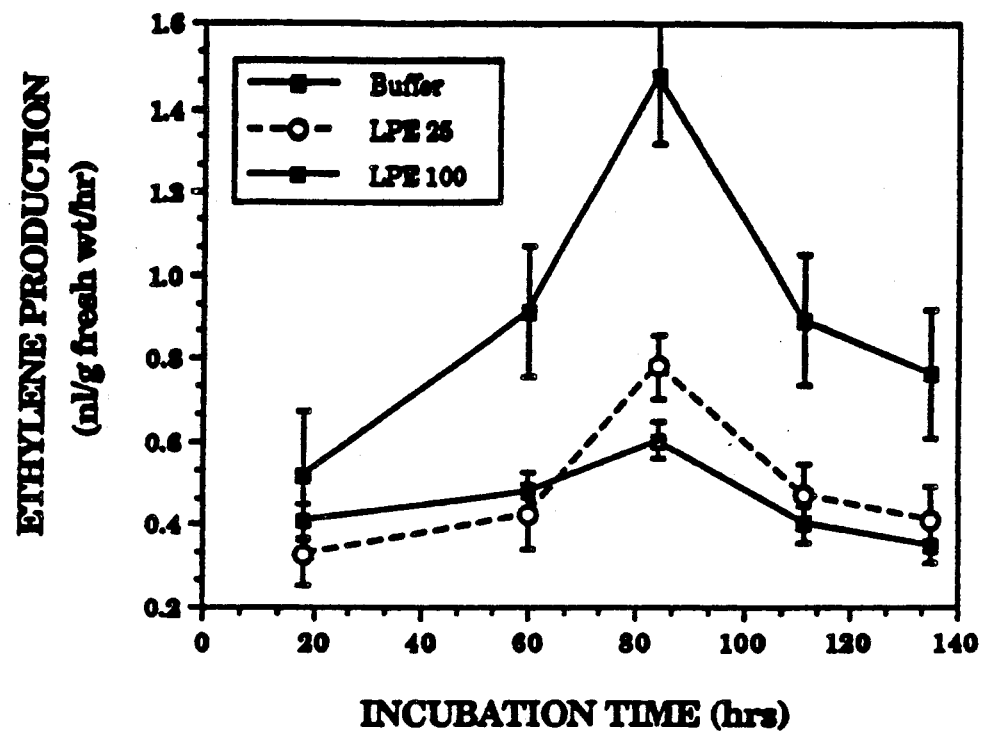
FIG. 1 is a graphical representation of the experimental results from Example 10 below illustrating the ethylene production in the treated fruit.

The present invention relates to the use of lysophospholipids and phospholipids containing ethanolamine in general, and lysophosphatidylethanolamine (LPE) in particular, as agents to achieve various biological effects on plants. The biological effects demonstrated by the application of such phospholipids, including LPE, include the enhancement of fruit ripening, inducement of ethylene production, decrease in fruit respiration so as to increase fruit storage life and firmness, and the decrease in the respiration of foliar tissue so as to maintain appearance and to delay or postpone senescence. The application of LPE has been found not only to achieve these effects when applied to growing plant tissue or fruits prior to harvest, but demonstrates similar effect on whole or sliced fruit after harvest and on other harvested plant tissues.

As used herein, phospholipids and lysophospholipids refer to the class of lipid compounds containing a phosphorus atom, a glycerol moiety, 0 to 2 fatty acid groups, and a nitrogenous base. Such phospholipids are considered derivatives of phosphatidic acid. Such phospholipids are wide spread in bacterial, animal, and plant tissues in which they are typically found in bilipid formations such as membranes and other sub-cellular structures. Such phospholipids are termed amphipathic compounds since they have both polar and non-polar regions thereby permitting their structures to associate with both hydrophilic and hydrophobic environments.

A preferred phospholipid within the practice of the present invention is lysophosphatidylethanolamine, or LPE. Phosphatidylethanolamine includes a pair of fatty acid components which may be saturated or unsaturated. LPE is derived from phosphatidylethanolamine by lysis of one fatty acid group therefrom. LPE is conventionally derived from egg yolk and is available commercially. Other related lysophospholipids, or phospholipids from which one fatty acid has been removed, are also useful within the present invention, with the preferred lysophospholipids being those which contain ethanolamine.

It has been found that the application of such phospholipids, and LPE, can be done to green tissues, to fruit prior to harvest, to fruit during post-harvest, or to excised tissues from fruit, all with beneficial effect. The beneficial effects can be enhanced by the presence of enhancement agents, such as ethanol or calcium chloride, although such devices may not be necessary to achieve the desired effects. Ethanol appears to act by enhancing the penetration of LPE while the enhancement activity of calcium chloride appears to be related to a metabolic function and perhaps an influence on membrane integrity. LPE has been found to have significant advantages when compared with other commercially available ripening agents, such as ethephon, in that LPE does not result in significant leaf die-off or other adverse effects on the green foliar tissue of the treated fruiting plant. It has also been found that LPE enhances the storage stability of harvested fruit so as to aid in its long term storage for commercially marketing.

As may be observed by reference to the examples below, LPE is effective at concentrations anywhere between 25 and 200 parts per million in the solution applied to the plant tissue. Suitable modes of treatment include spraying, dipping, soaking, and any other application in which the treating solution containing the effective agent LPE is applied to the plant material. The effective amount of application of other phospholipids may vary somewhat. For example it has been found that PDED may be suitably applied at 500 parts per million while LPS may be applied at rates analogous to LPE.

The exact manner in which the desired effects on fruit are caused by phospholipids in general, and LPE in particular, is not fully understood. It has been observed empirically that LPE stimulates ethylene production and suppresses respiration of plant tissues, but the exact mechanism for this phenomenon is not understood. It is possible, in view of the biological effects of such lipid molecules in biological tissues, that the effect is due to inner actions with the micro environment of the plant plasma membrane, or other cellular membranes, which might effect the binding of biologically active molecules, such as ethylene, to the appropriate receptor membranes. It is also possible that LPE may stimulate one or more of the cascades in the production of methionine, which is related to the enhanced production of ethylene. Another possibility is that LPE stimulates or modulates the activity of ethylene forming enzymes which are reported to be membrane bound enzymes. However, it is to be understood that the present invention is not limited to the methodology discussed above which is, in any event, merely speculative.

The efficacy and utility of the present invention will be better understood from the following examples.

EXAMPLE 1

Enhancement of Tomato Ripening in Field

This experiment was conducted to compare the effects of ethephon, a known fruit ripening agent, with lysophosphatidylethanolamine (LPE) in a field application to tomato. The tomato plants were of variety H.7155, a commercially important processing tomato variety. In conventional common practice, ethephon (tradename Ethrel) is often sprayed onto plants about 15 days prior to harvest to induce ethylene production and synchronized fruit ripening. In this experiment, ethephon was applied in an aqueous spray having 1000 parts per million (ppm) while LPE was applied at 100 ppm. Ethanol and tergitol were added, as indicated, at concentrations of 1% and 0.1% (v/v) respectively. Equivalent lengths of rows of standing tomato plants were sprayed with each treatment. The fruit was harvested 15 days after treatment. In the Table 1 below, the harvested fruit is listed as commercially graded. Grade A indicates well ripened, firm, but not green, fruit. The LPE plus ethanol treatment is listed twice, since it was applied to two different areas of the field.

TABLE 1

| Treatment | Grade A lbs | Grade A % | Green lbs | Green % | Rest lbs | Rest % | Total lbs |
|---|---|---|---|---|---|---|---|
| Ethephon, ethanol & tergitol | 22.25 | 41.9 | 5.50 | 10.20 | 26.00 | 48.40 | 53.75 |
| LPE & ethanol (1) | 26.25 | 42.70 | 16.75 | 27.20 | 18.50 | 30.10 | 61.50 |
| LPE & ethanol (2) | 40.00 | 56.30 | 14.75 | 20.80 | 16.25 | 22.90 | 71.00 |
| Ethephon | 28.50 | 53.30 | 10.25 | 19.20 | 15.25 | 28.50 | 53.50 |
| Ethephon & ethanol | 42.25 | 46.90 | 6.25 | 6.90 | 31.50 | 35.00 | 90.00 |
| Ethanol | 8.00 | 16.80 | 26.75 | 56.30 | 12.75 | 26.80 | 47.50 |
| Control | 9.25 | 18.40 | 23.50 | 46.80 | 17.50 | 34.80 | 50.25 |

These results indicated that LPE had a fruit ripening effect comparable to that of ethephon, even when the ethephon was enhanced with ethanol. In addition, for the LPE treatments, the rate of soft or overripe fruit was not increased. Thus ripening without softening, the most desirable effect, was indicated.

The tomatoes harvested from this experiment were then stored in boxes at room temperature for five days. The fruit was then subgraded to determine the marketable (i.e. firm) tomatoes at the end of that period as opposed to those which had become soft or rotted at this point. The results of this grading is summarized in the following Table 2.

TABLE 2

| Treatment | No. of Marketable Tomatoes (firm) | Soft or Rotted No. | Soft or Rotted % of Total |
|---|---|---|---|
| Ethephon, ethanol & tergitol | 99 | 17 | 14.66 |
| LPE & ethanol (1) | 129 | 6 | 4.44 |
| LPE & ethanol (2) | 108 | 9 | 7.69 |
| Ethephon | 74 | 21 | 22.11 |
| Ethephon & ethanol | 50 | 16 | 24.24 |
| Ethanol | 25 | 17 | 40.48 |
| Control | 35 | 16 | 31.37 |

These results indicated that the rate of softening of the fruit did not appear to be increased by LPE treatment. In fact, as can be seen above, the LPE treated tomatoes were better in this experiment than those from any of the other treatments. At a minimum, this result indicated no adverse effect on storage life of the fruit.

Another observation was made on the same plants. The leaves of the treated plants were examined four days after treatment and at harvest. The leaves were simply scored for color and vitality in general. The leaf appearances for the treatments are summarized in the following Table 3.

TABLE 3

| Treatment | Leaf Appearance (4 days) | Leaf Appearance (15 days) |
|---|---|---|
| Ethephon, ethanol & tergitol | Severe leaf burning | Dead |

TABLE 3-continued

| Treatment | Leaf Appearance (4 days) | Leaf Appearance (15 days) |
| --- | --- | --- |
| LPE & ethanol | Normal | Somewhat yellow |
| Ethephon | Brown | Dead |
| Ethanol | Normal | Somewhat yellow |
| Water (control) | Normal | Somewhat yellow |

The destruction of leaves of tomato is undesirable since then the fruit is exposed to sunlight which may scald the fruit. LPE treatment did not result in increased leaf senescence, as opposed to ethephon treatment which normally, as here, results in premature leaf death.

Tomatoes from two of these treatments, plus the control, were then placed in cold storage to investigate the effects of LPE treatment on storage life of the treated fruit. The rate of respiration of the fruit was measured as an indicating of the rate of fruit degradation. The fruit was stored in a cold room at about 3° C. for 40 days. All measurements were done in the cold room. The fruits were washed in cold distilled water for 10 seconds, put in cold jars, and incubated in the cold jars for 1 hour. Gas samples were then taken from the cold jars to analyze ethylene production and $CO_2$ evolution. After sampling, the jars were moved to room temperature conditions, allowed to equilibrate, and were then closed and incubated for 18 hours under continuous fluorescent light. Gas samples were again taken and analyzed for ethylene and $CO_2$. Four replicates were performed at each temperature. The results are summarized in the following Table 4.

TABLE 4

| Treatment | Rate of $CO_2$ Evolution at 3° C. (microliters/gram-hour) | Rate of $CO_2$ Evolution at 24° C. (microliters/gram-hour) |
| --- | --- | --- |
| Control (water) | 1.36 ± 0.08 | 10.50 ± 1.88 |
| Ethanol | 1.73 ± 0.13 | 14.32 ± 1.42 |
| LPE & ethanol | 0.79 ± 0.11 | 7.21 ± 1.20 |

This result indicated that even 40 days post-harvest, the LPE treatment had induced a lowered rate of respiration in the fruit, thus indicating a larger potential storage time for the fresh fruit.

EXAMPLE 2

Respiration of Leaves

Tomato plants of variety H.7155 were grown to two months of age in pots under fluorescent light in a growth room. The plants were then sprayed with either ethephon (at 100 or 1000 ppm) or LPE (at 50 or 100 ppm) solutions. Each solution also contained 1% ethanol by volume, which was also in the control.

Leaf samples were taken at 2, 4, 6 and 12 days after treatment and tested to determine their respiration rate. This sampling was done by excising the second pair of leaflets from leaves number 3, 4, 5 and 6 from the top of the plants on the sampling dates. The selected leaves were excised, rinsed with distilled water, and then stored for 1 hour to dissipate any ethylene caused by wounding and to gain full turgidity.

The leaves were surface sterilized with sodium hypochlorite (0.5% of 5% solution) for 1 minute, rinsed with autoclaved tap water, blotted dry with sterile tissue paper, and placed in a side arm flask with a serum septum. The flasks were then flushed for 10 seconds with filtered air and sealed with a rubber stopper. The treatment of the leaves was performed under a laminar air flow hood to assure sterility. The flasks were wrapped with aluminum foil and stored in the dark at room temperature. The amount of $CO_2$ evolution was measured by gas chromatograph. Two plants were sprayed with each treatment and four replicates were used with each treatment. On the days designated, leaves were taken from the plant and subjected to the $CO_2$ evolution testing process. For the plants treated with ethephon, all the leaves wilted within a few hours after treatment, and leaf damage was such that in two days measurements could not be taken. For the other leaves, the mean measured rate of respiration, as indicated by $CO_2$ evolution (in microliters/gram-hour), is given in Table 5 below.

TABLE 5

| Treatment | Respiration Rate at Day | | | |
| --- | --- | --- | --- | --- |
| | 2 | 4 | 6 | 12 |
| Ethanol | 195.25 ± 8.22 | 154.03 ± 6.23 | 139.17 ± 13.13 | 86.71 ± 4.12 |
| LPE (50 ppm) | 190.97 ± 4.92 | 152.35 ± 5.19 | 133.82 ± 11.23 | 80.81 ± 4.25 |
| LPE (100 ppm) | 166.05 ± 6.03 | 119.86 ± 8.76 | 100.87 ± 8.84 | 80.82 ± 3.89 |

Thus, the results indicated a significant decrease in the rate of respiration in the leaves even as the leaves stayed green and vigorous. The decrease in respiration was maintained over a long period and was concentration dependent. Thus the LPE treatment preserved the leaves and avoided the leaf senescence caused by the ethephon treatment.

EXAMPLE 3

Respiration of Leaves

Again tomato plants cv. H. 7155 were grown in pots for two and one-half months under fluorescent lights to serve as sources of leaf samples. The sample leaves were excised from the bottom pair of leaflets on the first side leaf after the branching top. The sampled leaf petioles were cut back to 1.5 cm, then the leaves were kept in glass jars, rinsed with distilled water and stored for 4 hours to dissipate wound effects and for full turgidity. Thereafter, the leaves were surface sterilized with sodium hypochlorite (0.5% of 5% solution) for 30 seconds, rinsed with autoclaved tap water and blotted dry.

The test leaves were then transferred to glass jars containing 15 milliliters of a treatment solution of LPE, or a control. The leaf petioles were dipped in the solutions and blotted dry.

The leaves were then removed, transferred to flasks which were flushed with filtered air and sealed. Again a laminar air flow hood was used for sterility. The flasks were wrapped with foil and incubated for 1, 2, 4 and 6 days from treatment. Respiration was measured by testing by gas chromatograph for $CO_2$ evolution. After each incubation, the leaves were transferred back to jars containing autoclaved tap water and kept under fluorescent light under the laminar air flow hood. Fresh water was added as needed. Three replicates were used for each treatment, each replicate including two leaflets.

In addition to LPE, one treatment utilized phosphatidyldimethylethanolamine dipalmitoyl, or "PDED." The results, with treatment and dosage, are given in Table 6 below.

TABLE 6

| Treatment | DAY: | | | | |
|---|---|---|---|---|---|
| | 0 | 1 | 2 | 4 | 6 |
| Control (Water) | 11.8.07 | 88.90 | 67.81 | 92.19 | 72.00 |
| LPE (10 ppm) | 80.13 | 83.56 | 61.54 | 83.52 | 61.27 |
| LPE (25 ppm) | 100.55 | 74.68 | 51.09 | 69.19 | 53.73 |
| LPE (50 ppm) | 87.66 | 81.54 | 50.36 | 68.42 | 45.62 |
| LPE (100 ppm) | 82.76 | 80.36 | 53.89 | 69.74 | 50.23 |
| LPE (200 ppm) | 76.27 | 84.92 | 52.60 | 59.37 | 45.02 |
| PDED (500 ppm) | 84.67 | 74.56 | 49.96 | 58.38 | 46.39 |

These results again reveal lowered respiration rates persistent over several days. It was also observed that the treated leaves had delayed senescence and retained vigor (color and turgidity) longer than the controls. The results also indicate that other glycerol lipid molecules have similar effects.

EXAMPLE 4

Cranberry in the Field

A plot of cranberry, variety Searles, in central Wisconsin, was treated by spraying with LPE (at 100 ppm), or a control in the middle of September. Four small (1 m by 1 m) plots were used for each treatment. The cranberries were harvested two weeks later by hand rake. Two samples were taken from each replication of 100 grams each to determine anthocyanin content and number of berries per 100 grams as an indicator of mean fruit size.

For the anthocyanin determination, 100 grams of berries were ground in a blender together with 100 ml of a mixture of 95% ethanol and 1.5M HCl (84:15, v/v). Duplicate samples of 5 ml of the resulting slurry were pipetted into centrifuge tubes with an additional 25 ml of the alcohol/HCl mixture and centrifuged at 16000 rpm for 5 minutes. The absorbence of the supernatant was read at 535 nm using a Beckman Spectrophotometer. Anthocyanin content was determined by the method of Fuleki and Francis *J. Food Science*, 32:72-77 (1968). The results of this experiment are presented in the following Table 7.

TABLE 7

| Treatment | Anthocyanin content (mg/100 g fruit) | Fruit size (Berries/100 g) |
|---|---|---|
| Control | 19.5 ± 0.58 | 90.6 ± 2.48 |
| LPE | 23.7 ± 0.72 | 89.8 ± 1.34 |

Thus it was found that LPE treatment enhanced ripening, as indicated by fruit color, without decreasing the mean fruit size significantly.

EXAMPLE 5

Application to Apple Fruit

Spraying of LPE treatment (100 ppm) and a control (water) was conducted on apple trees of variety Delicious and McIntosh. The fruit trees were sprayed in September and the fruit harvested one to two weeks later. Harvested fruit was stored in a cold room (3° C.).

Tests were conducted for both anthocyanin content and firmness for the McIntosh fruit. The anthocyanin test was conducted using only peels, using the alcohol/HCl and spectophotometric method as in Example 4. For the firmness test, fruit stored in the cold room for 5 months was then stored at room temperature for 4 days and the firmness was then tested with an Effegi pressure tester. The mean results are contained in the following Table 8.

TABLE 8

| Treatment | Anthocyanin content (mg/100 g fruit) | Firmness (lbs) |
|---|---|---|
| Control | 0.27 ± 0.02 | 6.92 ± 0.61 |
| LPE | 0.58 ± 0.07 | 8.00 ± 0.88 |

Thus the color of the fruit and its storage life were both indicated to be enhanced by the treatment.

To measure ethylene production and respiration, fruit from the cold room was surface sterilized with sodium hypochlorite, washed in cold distilled water, wiped dry, weighed and put in glass jars. Air was blown over the tops of the jars, which were then closed. The jars were sealed to light and stored in the cold room. Gas samples were retrieved from the jars after 10 minutes and 70 minutes for ethylene and $CO_2$ measurements. Twelve replications were performed. The results are summarized in the following Table 9.

TABLE 9

| | Delicious | | McIntosh | |
|---|---|---|---|---|
| Treatment | Ethylene (nl/g · hr$^{-1}$) | $CO_2$ (ul/g · hr$^{-1}$) | Ethylene (nl/g · hr$^{-1}$) | $CO_2$ (ul/g · hr$^{-1}$) |
| Control (water) | 13.38 ± 0.99 | 3.55 ± 0.38 | 41.40 ± 2.05 | 2.48 ± 0.69 |
| LPE | 11.74 ± 0.89 | 3.86 ± 0.26 | 41.88 ± 1.58 | 2.95 ± 0.32 |

Thus, although field observations of the sprayed fruit indicated a better fruit coloration, the ethylene production and respiration rates of the fruit were not significantly different from the control after 5 weeks of cold storage.

EXAMPLE 6

Storage of Apples Treated Post-Harvest

Untreated apples of varieties McIntosh, Delicious and Golden Delicious were harvested from the same orchard. Four to five apples of each variety were treated with either a citrate-phosphate buffer (pH 6.1) or the same buffer with LPE added at 100 ppm. The treatments were done by vacuum infiltration for 10 minutes at 26 inches of mercury. The fruits were then wiped with tissue paper and stored under a laminar air flow hood under fluorescent lighting at room temperature.

After 9 and 10 days of storage, fruit firmness was tested two different sides or cheeks of the fruit using an Effegi pressure tester. The measurement of total soluble solids were measured using a hand refractometer.

The firmness results are contained in Table 10 below. For each apple, the darker side was Side 1 (Blush for McIntosh, dark red for Delicious, yellowish for Golden Delicious) while the lighter side was Side 2 (Green for McIntosh, light red for Delicious, green for Golden Delicious). The results given are means for the test fruit.

TABLE 10

| Variety | Control | | LPE | |
|---|---|---|---|---|
| | Side 1 | Side 2 | Side 1 | Side 2 |
| McIntosh (9 days) | 5.50 ± .42 | 5.06 ± .21 | 6.81 ± .43 | 5.38 ± .24 |
| McIntosh (10 days) | 5.33 ± .34 | 5.83 ± .08 | 7.06 ± .39 | 6.38 ± .24 |
| Delicious (10 days) | 11.25 ± .49 | 10.75 ± .26 | 11.60 ± .59 | 12.25 ± .71 |
| Golden Delicious (10 days) | 9.05 ± .71 | 8.45 ± .54 | 9.10 ± .72 | 9.30 ± .91 |

These results indicated improved firmness, or increased storage value, for fruit even treated post-harvest. Similar tests were conducted for total soluble solids (in degrees Brix) on the same apples, and these mean results are listed in the following Table 11.

TABLE 11

| Variety | Control | | LPE | |
|---|---|---|---|---|
| | Side 1 | Side 2 | Side 1 | Side 2 |
| McIntosh (9 days) | 11.80 ± .57 | 11.60 ± .37 | 12.70 ± .81 | 11.80 ± .70 |
| McIntosh (10 days) | 12.30 ± .18 | 12.30 ± .40 | 11.80 ± 1.18 | 12.40 ± .77 |
| Delicious (10 days) | 12.64 ± .35 | 12.84 ± .26 | 13.84 ± .30 | 13.32 ± .27 |
| Golden (10 days) | 13.20 ± 1.13 | 13.12 ± .95 | 14.08 ± .27 | 13.52 ± .50 |

EXAMPLE 7

Post-Harvest Treated Apples

Intact, untreated McIntosh apples were tested. The test solutions were again citrate-phosphate buffer (pH 6.1) with or without LPE at 100 ppm. Again the treatment was by vacuum infiltration.

After treatment, the fruits were washed 10 times in tap water, surface sterilized with sodium hypochorite for one half minute, wiped dry and weighed. The apples were placed in a glass jar with 125 ml of the treatment solution and a vacuum to 26 inches of mercury was drawn for 10 minutes. The fruits were incubated in the jars under a laminar air flow hood with fluorescent lighting. Gas samples were taken at intervals. After each sample, the jars were opened and aerated with a fan. The air sample was tested for ethylene production and $CO_2$ evolution to test for respiration rate. The rate of ethylene production is listed below in Table 12 where ethylene production is in units of $nl/g \cdot hr^{-1}$ while incubation time is in hours.

TABLE 12

| | Ethylene Production | | | |
|---|---|---|---|---|
| | Incubation Time: | | | |
| Treatment | 22 | 44 | 69 | 94 |
| Control | 147.12 ± 12.04 | 86.96 ± 10.19 | 75.17 ± 43.45 | 87.04 ± 15.92 |
| LPE | 146.76 ± 11.08 | 106.22 ± 10.97 | 91.87 ± 7.10 | 108.18 ± 10.36 |

Table 13 lists the rate of $CO_2$ evolution in microliters/$g \cdot hr^{-1}$ for the same samples.

TABLE 13

| | $CO_2$ Evolution | | | |
|---|---|---|---|---|
| Treatment | Incubation Time: | | | |
| | 22 | 44 | 69 | 94 |
| Control | 13.19 ± .43 | 14.62 ± .44 | 7.87 ± .50 | 8.06 ± .68 |
| LPE | 10.85 ± .35 | 14.16 ± .60 | 6.94 ± .63 | 7.03 ± .48 |

This indicates that the apples which were treated had both increased ethylene production and decreased respiration rates than the control. The same apples were treated for total soluble solids and firmness in the same manner as in Example 6, with the results indicated in Table 14.

TABLE 14

| Treatment | Total Soluble Solids (°Brix) | | Firmness (lbs) | |
|---|---|---|---|---|
| | Blush | Green | Blush | Green |
| Control | 13.13 ± 1.05 | 12.33 ± 1.10 | 6.33 ± .33 | 6.67 ± .44 |
| LPE | 13.33 ± .82 | 11.60 ± .46 | 8.00 ± .29 | 7.00 ± .29 |

Thus it was found again that total soluble solids is largely unchanged while retention of firmness is improved. In fact, the lower value for total soluble solids on the green sides of the fruit support the perception of delayed ripening and senescence from the treatment.

EXAMPLE 8

Post-Harvest Treated Apples

Intact McIntosh apple fruit were harvested and treated in the citrats-phosphate buffer as in Example 7. The fruit was then tested for ethylene production, $CO_2$ evolution (respiration), and firmness as in Example 7. The treatment solutions in this experiment included the buffer alone as a control, LPE at 100 ppm, and each solution with 10 mM $CaCl_2$ added. The results of the tests of ethylene production are given in the following Table 15.

TABLE 15

| Treatment | Mean Ethylene Production ($nl/g \cdot hr^{-1}$) |
|---|---|
| Control (buffer) | 174.86 ± 7.51 |
| $CaCl_2$ | 178.51 ± 8.77 |
| LPE | 190.35 ± 12.74 |
| LPE & $CaCl_2$ | 200.84 ± 9.44 |

These results confirm increased ethylene production from LPE treatment and indicate that calcium chloride treatment increases the effect.

The measured rate of $CO_2$ evolution for the same treatments is summarized in Table 16.

TABLE 16

| Treatment | Mean Rate of $CO_2$ Evolution ($ul/g \cdot hr^{-1}$) |
|---|---|
| Control | 8.13 ± .32 |
| $CaCl_2$ | 7.96 ± .15 |
| LPE | 7.00 ± .40 |

TABLE 16-continued

| Treatment | Mean Rate of CO$_2$ Evolution (ul/g · hr$^{-1}$) |
|---|---|
| LPE & CaCl$_2$ | 7.58 ± .77 |

This demonstrates that in spite of increased ethylene production in the fruit, respiration rates are decreased by LPE treatment with or without CaCl$_2$ added.

The results of the tests, on the same fruit, for firmness are summarized in Table 17.

TABLE 17

| Treatment | Mean Blush Side Firmness (lbs) | Mean Green Side Firmness (lbs) |
|---|---|---|
| Control | 7.83 ± .22 | 5.92 ± 1.09 |
| CaCl$_2$ | 8.33 ± .22 | 7.50 ± .29 |
| LPE | 9.67 ± .22 | 7.50 ± .29 |
| LPE & CaCl$_2$ | 8.17 ± .44 | 6.67 ± .36 |

Again increased firmness in LPE treated fruit was demonstrated. While calcium chloride and LPE both acted to increase firmness, LPE alone seemed the most effective for this objective.

EXAMPLE 9

Treatment of Sliced Fruit Tissue

Mature apple fruit of variety Delicious was harvested. The fruit was washed 10 times in tap water, five times in deionized water, and then sterilized in sodium hypochlorite solution for 1 minute. The fruit was wiped dry, peeled, cut into slices of about 1.0 by 0.5 by 0.5 cm., blotted dry with tissue paper, and weighed. For each treatment, a total of 5 grams of fruit slices were used.

The fruit tissue slices were left under a laminar air flow hood for 3 hours to dissipate wound ethylene. The fruit sections were shaken by hand in flasks for 5 sec in treatment solutions of citrate-phosphate buffer, buffer with 100 ppm LPE, and buffer with 100 ppm LPS. After treatment, the treatment solutions were drained from the flasks, and the fruit pieces were put on sterile paper wipes to absorb excess solution. The flasks were also wiped with tissue paper, after which the fruit pieces were returned to the flasks. The tissues were then incubated sealed under fluorescent light. Four replications were performed for each treatment in addition to 4 repetitions of gas sampling. At the beginning of each incubation period, the flasks were flushed with filtered air, stoppered and re-introduced into incubation. The levels of ethylene and CO$_2$ in the gas samples were measured using a Shimadzu gas chromatograph with a flame ionization detector. The results of these measurements are listed in Tables 18 and 19, showing mean ethylene production (in ni/g·hr$^{-1}$) and mean CO$_2$ evolution (ul/g·hr$^{-1}$) respectively.

TABLE 18

| | Ethylene Production Time (hrs): | | | | |
|---|---|---|---|---|---|
| Treatment | 3 | 19 | 24 | 66 | 91 |
| Control | 22.16 ± .77 | 12.15 ± .82 | 10.30 ± .67 | 1.20 ± .09 | 2.76 ± .34 |
| LPE | 24.37 ± .25 | 15.84 ± .73 | 12.82 ± .21 | 2.51 ± .29 | 5.68 ± .58 |
| LPS | 23.34 ± .76 | 14.81 ± .76 | 10.47 ± .65 | 2.00 ± .20 | 5.81 ± .80 |

TABLE 19

| | CO$_2$ Evolution Time (hrs): | | | | |
|---|---|---|---|---|---|
| Treatment | 3 | 19 | 24 | 66 | 91 |
| Control | 20.98 ± .77 | 20.68 ± 1.02 | 19.63 ± .94 | 27.66 ± 2.17 | 26.08 ± 3.09 |
| LPE | 20.50 ± .46 | 17.40 ± .34 | 18.80 ± .49 | 24.84 ± 1.0 | 23.72 ± 2.50 |
| LPS | 19.26 ± 1.22 | 18.98 ± .62 | 18.14 ± 1.66 | 27.82 ± 2.24 | 25.58 ± 3.53 |

These results confirmed ethylene stimulation and respiratory suppression by LPE treatment. The stimulation of ethylene with LPS was demonstrated, although suppression of respiration was not clearly demonstrated with LPS treatment.

EXAMPLE 10

Treatment of Sliced Fruit

Fruit of cranberry variety Searles were tested. The fruit was washed and sterilized as in Example 9. The deseeded cranberry fruits were halved. The halved fruit was left under a laminar air flow hood for 3 hours to dissipate wound ethylene. Treatment solutions were introduced into flasks with the fruit, and shaken by hand for 5 seconds. The fruit was dried, the flasks were wiped, and the fruit was incubated in the flasks sealed under fluorescent lighting. Three replications were used for each treatment, with three air samples per replicate. Before each incubation period, the flasks were flushed with filtered air.

Figure 2:
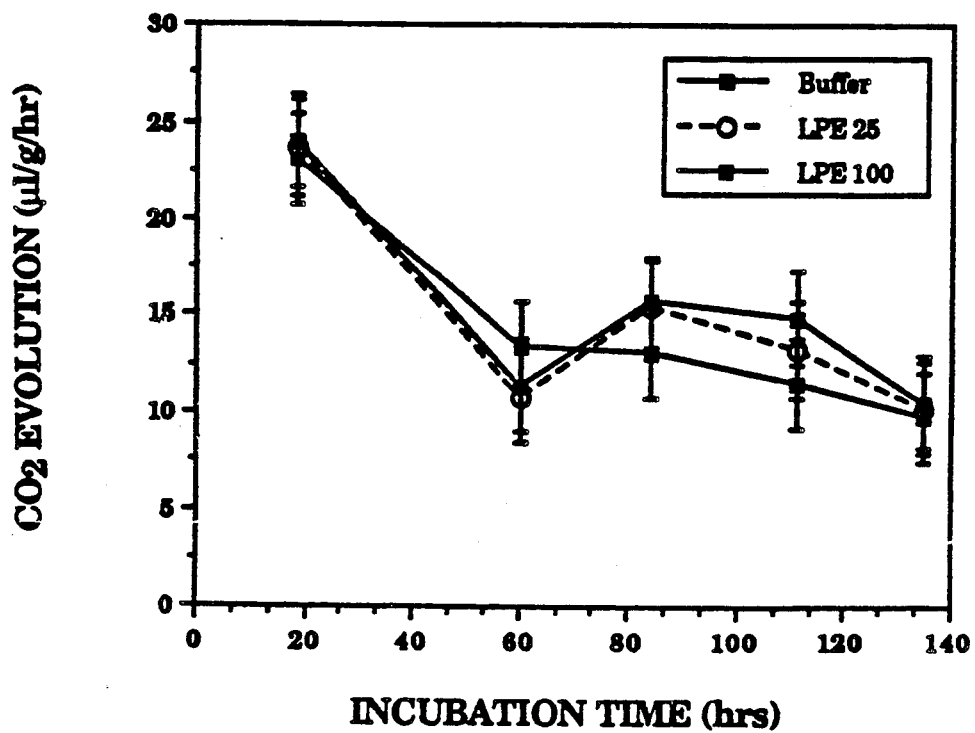
FIG. 2 is a graphical representation of experimental results, also from Example 10 below, of carbon dioxide evolution in the treated fruit.

The results of the measurements of mean ethylene production and mean CO$_2$ evolution are charted in FIGS. 1 and 2 respectively. The replicates were at treatment levels of 25 and 100 ppm as indicated. This confirms in cranberry the effect of stimulation of ethylene production as demonstrated in apples, although respiration did not seem as affected in cranberry.

It is to be understood that the present invention is subject to such modifications and variations thereof as come within the scope of the following claims.

We claim:

1. A method of enhancing the ripening and storage stability of fruit after harvest comprising the step of treating the fruit after harvest with a treatment comprising an amount of an agent effective to enhance fruit ripening and stability, the agent selected from the group consisting of a lysophospholipid and a phospholipid containing ethanolamine.

2. A method for enhancing the storage life of green plant foliage after harvest comprising the step of applying a treatment solution to the foliage after harvest comprising an amount of lysophosphatidylethanolamine effective to delay senescence and to enhance the storage stability of the foliage.

3. A method as claimed in claim 1 wherein the fruit is apple.

4. A method as claimed in claim 1 wherein the fruit is tomato.

5. A method as claimed in claim 1 wherein the fruit is cranberry.

6. A method as claimed in claim 1 wherein the treatment further includes an enhancer selected from the group consisting of ethanol and calcium chloride.

7. A method of increasing the stability in storage of harvested fruit comprising treating the harvested fruit with a treatment solution comprising a carrier and an amount of an agent effective to enhance the storage stability of the fruit, the agent selected from the group consisting of a lysophospholipid and a phospholipid containing ethanolamine.

8. A method as claimed in claim 7 wherein the agent is selected from the group consisting of lysophosphatidylethanolamine, phosphatidyldimethylethanolamine dipalmitoyl, and lysophosphatidylserine.

9. A method as claimed in claim 7 wherein the fruit is selected from the group consisting of apple, tomato, and cranberry.

10. A method as claimed in claim 7 wherein the treatment further includes an enhancer selected from the group consisting of ethanol and calcium chloride.

11. A method of enhancing the ripening and the storage stability of fruit comprising the step of treating the fruit with an amount of lysophosphatidylethanolamine effective to enhance fruit ripening and stability.

12. A method as claimed in claim 11 wherein the fruit is selected from the group consisting of apple, tomato, and cranberry.

13. A method as claimed in claim 11 wherein the lysophosphatidylethanolamine is present in the treatment at a level of between 25 and 200 parts per million.

14. A method of increasing the stability in storage of harvested fruit comprising treating the harvested fruit with a treatment solution comprising a carrier and an amount of lysophosphatidylethanolamine effective to enhance the storage stability of the fruit.

15. A method as claimed in claim 14, wherein the fruit is selected from the group consisting of apple, tomato, and cranberry.

16. A method as claimed in claim 14 wherein the lysophosphatidylethanolamine is present in the treatment solution at a level of between 25 and 200 parts per million.

17. A method for enhancing the storage life of green plant foliage comprising the step of applying a treatment solution to the foliage comprising an amount of lysophosphatidylethanolamine effective to delay senescence and to enhance the storage stability of the foliage.

18. A method for enhancing the storage life of harvested plant material comprising the step of applying a treatment solution to the plant material comprising an amount of lysophosphatidylethanolamine effective to delay senscence and to enhance the storage stability of the plant material.

19. A method for enhancing the storage life of harvested plant material comprising the step of applying a treatment solution to the plant material comprising an amount of an agent effective to enhance the storage life of the material, the agent selected from the group consisting of a lysophospholipid and a phospholipid containing ethanolamine.

* * * * *